(12) United States Patent
Lejars et al.

(10) Patent No.: US 8,492,524 B2
(45) Date of Patent: Jul. 23, 2013

(54) METHOD FOR EXTRACTING A PROTEIN FROM MILK

(75) Inventors: Alain Lejars, Pierres (FR); Michel Nogre, Vanves (FR); Monique Ollivier, Le Kremlin Bicetre (FR)

(73) Assignee: LFB Biotechnologies, Les Ulis (FR)

( * ) Notice: Subject to any disclaimer, the term of this patent is extended or adjusted under 35 U.S.C. 154(b) by 70 days.

(21) Appl. No.: 12/520,826

(22) PCT Filed: Jan. 2, 2008

(86) PCT No.: PCT/FR2008/000007
§ 371 (c)(1),
(2), (4) Date: Jun. 22, 2009

(87) PCT Pub. No.: WO2008/099077
PCT Pub. Date: Aug. 21, 2008

(65) Prior Publication Data
US 2009/0281283 A1 Nov. 12, 2009

(30) Foreign Application Priority Data
Dec. 29, 2006 (FR) ...................................... 06 11536

(51) Int. Cl.
*C07K 14/745* (2006.01)
*A23C 9/148* (2006.01)
*A23J 1/20* (2006.01)

(52) U.S. Cl.
USPC ............................. 530/381; 530/417; 426/491

(58) Field of Classification Search
USPC .................................. 530/381, 417; 426/491
See application file for complete search history.

(56) References Cited

U.S. PATENT DOCUMENTS

| | | | |
|---|---|---|---|
| 4,229,342 | A | 10/1980 | Mirabel |
| 4,519,945 | A | 5/1985 | Ottenhof |
| 5,827,690 | A | 10/1998 | Meade et al. |
| 5,849,992 | A | 12/1998 | Meade et al. |
| 5,880,327 | A | 3/1999 | Lubon et al. |
| 6,046,380 | A | 4/2000 | Clark |
| 6,183,803 | B1 | 2/2001 | Morcol et al. |
| 6,255,554 | B1 | 7/2001 | Lubon et al. |
| 6,268,487 | B1 | 7/2001 | Kutzko et al. |
| 6,984,772 | B1 | 1/2006 | Velander et al. |
| 7,045,676 | B1 | 5/2006 | Gordon et al. |
| 7,247,331 | B2 | 7/2007 | Souppe |
| 2004/0117862 | A1* | 6/2004 | Cooper et al. .................... 800/7 |
| 2004/0219225 | A1 | 11/2004 | Kivits et al. |
| 2005/0272917 | A1 | 12/2005 | Jiao et al. |
| 2006/0040025 | A1 | 2/2006 | Souppe |
| 2008/0044544 | A1 | 2/2008 | Souppe |
| 2009/0281283 | A1* | 11/2009 | Lejars et al. .................. 530/381 |

FOREIGN PATENT DOCUMENTS

| | | |
|---|---|---|
| EP | 0200421 | 11/1986 |
| EP | 0264166 | 4/1988 |
| EP | 0 527 063 | 2/1993 |
| EP | 0 741 515 | 11/1996 |
| EP | 0807170 | 11/1997 |
| EP | 1 739 170 | 1/2007 |
| FR | 2841747 A1 | 1/2004 |
| WO | WO-96/03051 | 2/1996 |
| WO | WO-2004/076695 | 9/2004 |
| WO | WO-2005/089040 A | 9/2005 |

OTHER PUBLICATIONS

Cox DA, Bürk RR: "Isolation and characterisation of milk growth factor, a transforming-growth-factor β2-related polypeptide, from bovine milk," Eur J. Biochem., vol. 197, 1991, pp. 353-358, XP002440848 "Materials and Methods" p. 353-354.
Devinoy et al., Nucleic Acids Research vol. 16, No. 6 (Aug. 25, 1988, p. 8180). (abstract only included).
Pall Life Sciences Product Note; "MEP HyperCel Mixed-Mode Chromatography Sorbent—Hydrophobic Charge Induction Chromatography/HCIC"; www.pall.com/biopharm; 2009; 9 pages.
Ringier Article; "Pall to expand proteomics technology R&D line"; www.industrysourcing.com; Jan. 14, 2005; 3 pages.
"Biopharmaceutical equipment and purification techniques", img. duxiu.com/n/printing.htm, p. 12, www.yishuleia.cn/n/printing.htm, (2003), p. 13 (Chinese and English translation).
Parks, "Cholesterol Esters of Skim Milk", Journal of Dairy Science, vol. 63, No. 2, Feb. 1980, pp. 295-297.

* cited by examiner

*Primary Examiner* — Chih-Min Kam
(74) *Attorney, Agent, or Firm* — Harness, Dickey & Pierce, P.L.C.

(57) ABSTRACT

The invention relates to a method for extracting a protein from milk, having at least one hydrophobic pocket and a negative charge to the natural pH of milk, that comprises the following steps: a) skimming and delipidation of the milk; b) passing the delipidated and skimmed fraction containing the protein on a chromatographic substrate on which is grafted a ligand having both a hydrophobic characteristic and an ionic characteristic in pH conditions enabling the protein to be retained on the substrate, the pH being higher than 4.6; c) elution of the protein; d) purification of the eluted fraction by removing the milk proteins from the eluted fraction; and e) recovering the protein.

23 Claims, 1 Drawing Sheet

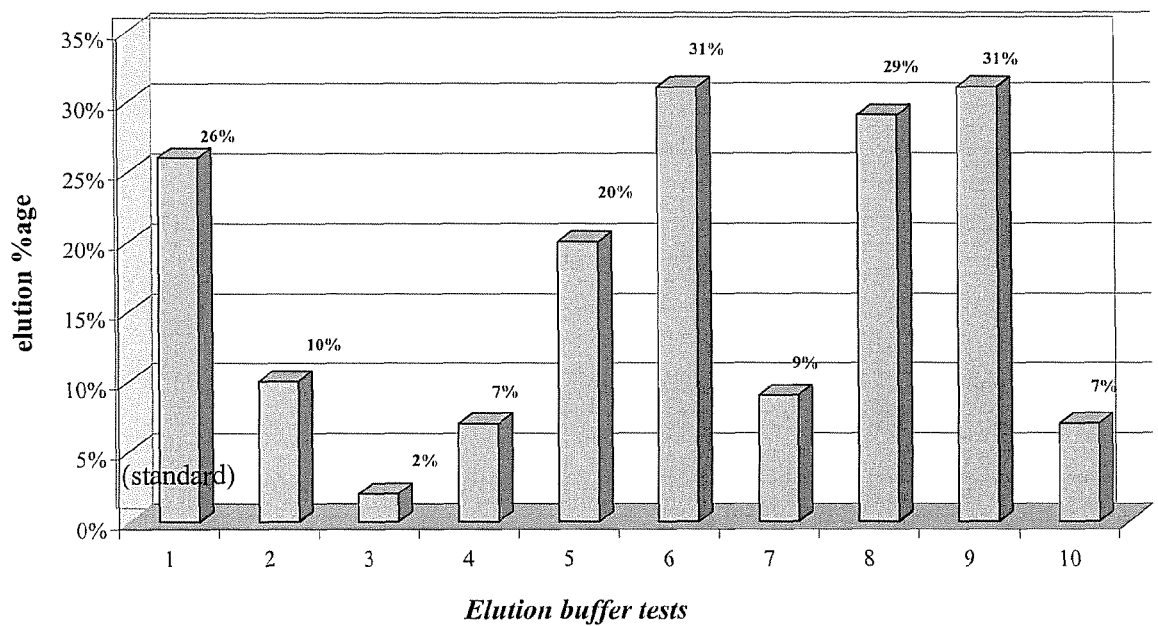

METHOD FOR EXTRACTING A PROTEIN FROM MILK

CROSS-REFERENCE TO RELATED APPLICATIONS

This application is a National Phase Entry of International Application No. PCT/FR2008/000007, filed on Jan. 2, 2008, which claims priority to French Patent Application No. 06 11 536, filed on Dec. 29, 2006, both of which are incorporated by reference herein.

BACKGROUND AND SUMMARY

The present invention relates to a process for the extraction of one or more proteins, particularly globular proteins the tertiary structure of which forms a hydrophobic patch and that are present in milk, using a support to which is bound a ligand that is simultaneously hydrophobic and ionic.

The majority of the commercially available medications consist of chemical substances obtained by synthesis. In fact, until recently, modern medicine has relied heavily on medications produced through chemical synthesis for the treatment or diagnosis of diseases. However, proteins represent a significant part of the molecules that carry biological information. This is the case, in particular, with a large number of hormones, growth factors, blood coagulation factors, and even antibodies.

Generally speaking, proteins are polymers consisting of amino acids, usually with a high molecular weight, and that cannot be obtained at reasonable costs through chemical synthesis. Such proteins intended for therapeutic use are usually isolated and purified from, for example, living organisms, tissues, or human or animal blood. This is particularly the case with insulin, which is extracted from pork pancreas; coagulation factors, such as factor VIII or factor IX, which are extracted from blood plasma; and immunoglobulins.

However, although the processes for the preparation of the foregoing proteins are widely used today, they have disadvantages. The low content of certain proteins extracted from blood platelets precludes their isolation in sufficient quantities to meet ever-increasing therapeutic needs. Furthermore, the presence of viruses, prions, or other pathogens in plasma makes it necessary for the plasma-protein manufacturing processes to include additional viral neutralisation and/or viral elimination steps in order to obtain such products that can be used for therapeutic purposes.

In order to remedy these disadvantages, recourse has been made to genetic engineering, a technique that is likewise widely used for the synthesis of a protein from an isolated gene that is transferred into a cell, which then performs the secretion of the protein in question. Such a protein, obtained outside its own original cell system, is known as a "recombinant" protein. According to this technique, various cell systems can be used.

Bacterial systems, such as for example *E. coli*, are very widely used and very effective. They make it possible to produce recombinant proteins at a low cost. Nevertheless, such systems are limited to the preparation of simple, non-glycosylated proteins, which do not require elaborate folding processes.

Fungal systems are also used for the production of secreted proteins. The disadvantage of such fungal systems lies in the fact that they give rise to post-translational modifications, consisting, for example, of a graft of glycan units and sulfate groups, which strongly affect the pharmacokinetic properties of the resulting proteins, particularly through the addition of various groups of mannose derivatives. Systems that use baculoviruses make it possible to produce a broad variety of proteins, such as vaccinal proteins or growth hormones; however, their industrial application has not been optimised.

Mammalian cells are also grown in the preparation of complex recombinant proteins, such as monoclonal antibodies. Cell expression systems lead to properly folded and modified recombinant proteins. The low yield in relation to the cost of production is a major disadvantage. As an alternative to such cell systems, transgenic plants are employed in order to obtain proteins in significant quantities. However, these systems entail plant-specific post-translational modifications, particularly through the addition, to the resulting proteins, of highly immunogenic xylose residues, thereby limiting their use for therapeutic purposes.

One alternative to the above-mentioned cell systems consists of using transgenic animals for the production of recombinant vaccines or complex therapeutic proteins. The resulting proteins exhibit a glycosylation that is very similar to that of human beings, and are properly folded. These complex proteins do not consist merely of a single polypeptide chain, such as, for example, growth hormone; instead, they are modified in various ways after assembly of the amino acids, particularly through specific cleavages, glycosylations, and carboxymethylations. In the great majority of cases, such modifications cannot be performed by bacterial cells or yeasts. Conversely, transgenic animals make it possible to combine both the levels of expression found in bacterial cell systems and the post-translational modifications obtained using cell cultures, all at production costs that are lower than the costs incurred through the use of cell expression systems.

Among the biological materials of transgenic animals, milk has been the subject of studies that have led it to be considered a very satisfactory secretion source for recombinant proteins. The recombinant proteins produced from milk of transgenic animals can easily be obtained by grafting the gene that codes for the desired protein, to the regulatory region of one of the milk protein-synthesis genes that will direct this protein specifically to the mammary gland, and then its secretion in the milk.

As an example, reference may be made to European patent application No. EP 0 527 063, which describes the production of a desired protein in the milk of a transgenic mammal, in which the expression of the gene that codes for the desired protein is controlled by a whey protein promoter. Other patents or patent applications describe the preparation of antibodies (EP 0 741 515), collagen (WO 96/03051), human factor IX (U.S. Pat. No. 6,046,380), and factor VIII/von Willebrand factor complexes (EP 0807 170) in the milk of transgenic mammals. Despite the satisfactory results of these methods in terms of protein expression, the use of milk as a source of recombinant proteins has disadvantages. The major disadvantage lies in the difficulties, on the one hand, of extracting them from the milk with a satisfactory yield, and, on the other hand, of purifying them afterward.

In fact, milk is a mixture that consists of 90% water and of various other constituents that can be divided into three categories. The first category, known as "lactoserum" (or whey), consists of carbohydrates, soluble proteins, minerals, and water-soluble vitamins. The second category, known as the "lipid phase" (or cream), contains fatty materials in the form of an emulsion. The third category, known as the "protein phase", consists of approximately 80% caseins, which form a group of proteins that can be precipitated at pH 4.6 or through the effect of rennet, an enzymatic coagulant, in the presence of calcium. The various caseins form a colloidal micellar complex that can reach diameters on the order of 0.5 µm, with phosphocalcic salts that can be present, for example, in the form of aggregates ("clusters") of tricalcium phosphate, i.e. $Ca_9(PO_4)_6$. Such micelles consist of casein subunits made of a hydrophilic layer rich in κ-casein surrounding a hydrophobic core, with the phosphocalcic salts being bound to the hydrophilic layer through electrostatic interactions. These phosphocalcic salts may also be present in the internal volume of the micelle, without being bound to the casein. This protein phase also contains soluble proteins, such as lactalbumins and lactoglobulins, as well as albumins and immunoglobulins from blood.

Depending on the nature of the recombinant protein secreted in the milk of transgenic animals, the protein may be present either in the lactoserum or in the protein phase, or even in both of them simultaneously. The richness and complexity of each category of milk constituents make it even more difficult to implement an extraction of the protein, particularly the one trapped in the casein micelles. Another difficulty lies in the fact that the predominance of this protein in either of the two phases cannot be predicted with certainty.

A recombinant protein may also exhibit affinities for the calcium ions in the milk, which are present in the form of salts and/or various soluble complexes, or in the form of phosphocalcic salts of the casein micelles. These affinities are reflected by electrostatic bonds between the protein and the divalent calcium cations. The protein/calcium ion affinities make it possible to define the affinity constants, which, depending on their value, determine the strength of the bond. Generally speaking, the majority of the proteins that have an affinity for calcium ions are bound to the phosphocalcic salts of the micelles. Their extraction requires the implementation of complex steps, with the corresponding problems of implementation and yield. The classical solution used in the dairy industry to isolate the proteins, which consists of pasteurisation, followed by enzymatic coagulation or acid precipitation (at pH 4.6), cannot be applied in this case, because the recombinant proteins are often denatured due to the combined effect of the temperature and pH. Furthermore, the trapping of the proteins in the casein micelles leads to low extraction yields. Other solutions, consisting of implementing physical methods for fractionating the milk using filtration, centrifuging, and/or sedimentation or precipitation techniques, also lead to unacceptable extraction yields and to low-purity extracted recombinant proteins.

The document EP 0 264 166 describes the secretion of a desired protein in the milk of genetically modified animals. This document does not mention any steps for the purification of this protein from the milk. U.S. Pat. No. 4,519,945 describes a process for the extraction of a recombinant protein by preparing a precipitate of caseins and lactoserum from milk, with the implementation of acidification and heating steps, as mentioned above. This process results in a significant loss of activity of the protein in question and a low extraction yield.

U.S. Pat. No. 6,984,772 discloses a process for the purification of recombinant fibrinogen from the milk of a transgenic mammal. This process includes a step consisting of separating the lactoserum from the casein pellet and protein phase by means of successive centrifuging operations. The lactoserum is isolated and then stored for the rest of the process, which gives a purified fibrinogen solution. However, this process cannot be applied to the production, with a satisfactory yield, of recombinant proteins that are trapped in and/or on the casein micelles, such as plasma coagulation factors, e.g. factor VII, factor VIII, and factor IX.

Patent application No. WO 2004/076695 describes a process for the filtration of recombinant proteins from the milk of transgenic animals. This process includes an initial milk clarification step, i.e. a step consisting of removing the constituents of the milk so as to obtain a solution capable of being filtered through a filter membrane the pores of which have a diameter of 0.2 μm. Such a step leads to the removal of casein micelles. Consequently, the implementation of this step may be prohibitive, in terms of yield, if the casein micelles are capable of containing a desired protein trapped inside their structure.

U.S. Pat. No. 6,183,803 describes a process for the isolation of proteins that are naturally present in milk, such as lactalbumins, and of recombinant proteins, such as human albumin or α1-antitrypsin, from milk. This process includes an initial step consisting of placing a chelating agent in contact with the milk containing a desired protein. This step causes the disruption of the casein micelles, which in turn leads to the formation of a clarified milk serum containing the casein, the lactoserum proteins, and the desired protein. The process then includes a step consisting of the structural re-formation of the casein micelles through the addition of insoluble divalent cation salts to the liquid support (i.e. the clarified milk serum). These micelles precipitate, leading to the formation of a liquid phase that includes the desired protein, which is not trapped in the micelles, because the salts saturate the electrostatic binding sites of the caseins. Thus, according to this process, the separation of the desired protein is finally achieved through the structural re-formation of the micelles and their precipitation. This process is complex and difficult to implement, and cannot be applied to proteins that have a relatively high affinity for calcium ions. Coagulation proteins, including, in particular, those that are known to be synthesised under the effect of vitamin K, fall into this category.

Starting from two observations—namely, that the processes for the separation and purification of certain categories of recombinant proteins, that are secreted in the milk of transgenic animals and that are present in lactoserum lead to very low yields, and processes of other categories of proteins, that are trapped in casein micelles, are complex and difficult to implement—the present applicant set herself the objective of providing a process for the extraction, from milk, of proteins that are constituents of milk, whether natural or otherwise, such as recombinant factor VII, factor VIII, and factor IX, which in particular exhibit an affinity for the ionic forms of calcium in the milk, which process can be implemented in a simple way, with a satisfactory production yield, and preserves the biological activity of the protein. It was with the goal of addressing this technical problem that the present applicant developed a process for the extraction of a protein that is present in milk, which protein has at least one hydrophobic patch and a negative charge at the natural pH of milk, including the following steps consisting of:

a) skimming and defatting of said milk,
b) transferring the defatted and skimmed fraction containing said protein to a chromatographic support onto which is grafted a ligand that is simultaneously hydrophobic and ionic, under pH conditions allowing said protein to be captured on said support, said pH being higher than 4.6,
c) eluting the protein,
d) purifying the eluted fraction by removing the milk proteins from said eluted fraction, and
e) recovering said protein.

The process according to the invention is advantageous in that it is very easy to implement, because, on the one hand, it contains only a few steps, and, on the other hand, it does not necessarily require the implementation of a milk clarification step prior to the implementation of the first step for the capture of the desired protein on the support onto which the ligand is grafted. The process according to the invention may be applied to fresh milk or frozen milk. The milk may be milk from any female mammal that contains a desired protein, such as a cow, ewe, goat, rabbit, mouse, rat, or sow, which list is not limitative.

Depending on the natural fluidity of the mammalian milk in question, it may be advantageous to fluidise the milk prior to the skimming and defatting step. As an example, reference may be made to rabbit milk, which, being fairly dense, is advantageously fluidised for an easier implementation of the invention. However, even in the case of fairly dense milks, the fluidisation step is purely optional. This fluidisation step may be performed by adding an aqueous solvent to the raw milk. For example, the aqueous solvent may be a phosphate salt based solution with a concentration lower than 100 mM, the pH of which is comprised between 7.5 and 8.5, preferably between 8.0 and 8.3, such as a 30 mM sodium phosphate solution, pH 8.0, which list is not limitative. Such an aqueous solvent may also contain sodium chloride, the maximum concentration of which is about 40 mM. Such solutions maintain the stabilised micellar structure of the milk (casein micelles in suspension).

For the purposes of the invention, the term "skimming" shall be understood as referring to the separation of the fatty matter of the milk, so as to obtain two fractions, i.e. the skim milk and the cream. Skimming is a technique that is well known to those skilled in the art, and can be performed, for example, using a skimmer or by means of organic solvents such as trichloroacetic acid, which is not limitative. In one particular embodiment, the skimming of the milk is performed by filtration through a glass fiber support with a positive zeta potential. As an example of such a filter, reference may be made to the Ultipor® GF Plus filter as well as to HP serie Supradisk filters or AKS active charcoal serie (Pall Life Science), GF filters (whatman), VR Zetaplus filters or Delipid filters (Cuno 3M). The Ultipor® GF Plus filter (Pall) with a 1 µm threshold and the deep filter VR02 or VR04 (Pall) are advantageously used.

This filtration step also makes it possible to de-fat the fraction, that is, to remove the lipids, such as the fatty acids, glycerides, and sterols. This defatting can be accomplished via frontal filtration of the milk through the Ultipor® GF Plus filter after having allowed the diluted milk to stand for 30 minutes (such that the fatty matter floats to the surface, thereby optimising the separation of the cream from the milk).

This skimming and defatting step is essential because the ligand grafted onto the support, which ligand is simultaneously hydrophobic and ionic, adsorbs lipids. Therefore, the lipids must be removed prior to step b), because otherwise, the desired protein cannot be retained by the ligand, or can be retained only poorly. The result of such a situation would be a reduction in the yield of the process for the extraction of the desired protein. One of the advantageous aspects of the invention is the fact that the fraction resulting from step a), which has simply been skimmed and defatted, is directly suitable for the implementation of step b), which very advantageously is a step of purification via affinity chromatography. Thus, no intermediate step is strictly necessary in order to render the defatted and skimmed fraction suitable for purification via affinity chromatography in step b).

Step b) should not be performed at a pH that is lower than the isoelectric point (pI) of the caseins, which is between 4.6 and 5. In fact, if step b) is implemented at a pH that is lower than the pI of the caseins, the latter will precipitate, thereby entailing the risk of causing significant damage to the chromatographic support. In particular, when the chromatography step is performed with the use of a column, the precipitation of the caseins may clog the column, thereby damaging the column and its contents, i.e. the chromatography gel. Furthermore, at a pH lower than 4.6, it is also likely that other proteins will precipitate, such as, for example, transferrin or albumin, which could give rise to reduced yields. Last, certain proteins are denatured at an acid pH. This is the case, for example, with factor VII, factor VIII, factor IX, fibrinogen, and complement factor H, which list is not limitative.

Step b) is advantageously performed at a pH between 5 and 8.5. The skimmed and denatured milk produced in step a) is thus applied to the chromatographic support in step b) at a pH between 5 and 8.5. This pH is advantageously between 5.5 and 8, or between 6 and 7.5. This pH is preferably between 6.5 and 6.8. This pH is more preferably the natural pH of the milk.

At such a pH (that is, at a pH between 5 and 8.5), the proteins that have natural interaction sites, such as, for example, the proteins that have an antigen/antibody, enzyme/substrate, or enzyme/inhibitor affinity or pseudoaffinity, which list is not limitative, naturally have their charges and hydrophobic regions in relative positions with respect to one another, and do not vary widely between pH 5 and pH 8.5. Therefore, at this pH, these proteins are negatively charged. Advantageously, at this pH, the interactions between the ligand and the protein are essentially hydrophobic reactions.

The chromatography technique advantageously used in the process according to the invention allows the defatted and skimmed fraction containing the desired protein to be captured on a support onto which is grafted a ligand that is simultaneously hydrophobic and ionic. Surprisingly, such a ligand makes it possible to bind the desired proteins that, because of their structure, have a hydrophobic patch, while leaving the impurities, including the casein micelles, unbound. The internal hydrophobic regions of the proteins can bind to this kind of ligand, and will allow interactions with the desired protein, thereby ensuring a high affinity for the desired protein and increased selectivity for the proteins to be purified.

The unbound proteins consist essentially of the majority of the caseins, whey acid protein (WAP), transferrin, lactoglobumins, lactalbumins, and serum albumins. Furthermore, this process is suitable for the extraction of any protein that has the designated characteristics: that is, at the natural pH of the milk, i.e. within the range from approximately 6.5 to 6.8, the protein has hydrophobic regions and carries negative charges; or, at the very least, the overall balance of the charges very advantageously favours the negative charges.

Within the scope of the invention, the pH conditions allow the protein to be retained by—or, generally speaking, to bind to—the ligand of the chromatographic support, either through hydrophobic interactions or through electrostatic interactions as well as through hydrophobic interactions. Such conditions depend to a large extent on the isoelectric point of the protein to be purified, and therefore on the pH at which the process is implemented. A chromatographic support that may be used is a support having a positively charged ligand (of the anion-exchange type), and the pH may be adapted such that the protein carries an overall negative charge. Conversely, a negatively charged ligand may be used when the process is performed at the pH that is advantageously used for the implementation of the invention, i.e. between 5 and 8.5. The terminal functional group of this ligand may be, for example, a sulfonyl or carboxyl group, and the pH may be set at a value greater than 6, so that the protein has an overall positive charge. This embodiment is applicable when the isoelectric point of the protein to be purified is such that, at a basic pH, in particular at a pH greater than 6, the protein has a positive charge. Care should also be taken to ensure that the pH is compatible with the implementation of the process, so as not to damage significantly the proteins to be extracted, or the milk.

In another embodiment, the pH at which step b) is implemented is between 5 and 8.5, and the pH value is selected in such a way that the interactions between the protein and the ligand are essentially hydrophobic. The implementation of step c) (elution) may be performed using any eluent known to those skilled in the art that allows the protein to cease to be retained due, for example, to ionic repulsion effects but also to chaotropic effects. The elution preferably involves ionic repulsion effects. The structural form of the proteins and the charge of the proteins can be modified by adjusting the pH of the elution buffer, or by selecting a suitable elution buffer.

Before the implementation of step b), the chromatographic support is preferably equilibrated with a solution (loading buffer) based on a phosphate salt with a concentration lower than 100 mM, the pH of which is comprised between 7.5 and 8.5, preferably between 8.0 and 8.3, such as a sodium phosphate solution from 20 to 30 mM, pH 8.0. Such a solution may also contain sodium chloride, the maximum concentration of which is about 100 mM, and preferably in the range from 20-60 mM. Such a solution may also be based on citrate salt, in particular trisodium citrate 0.20-0.30 M, preferably 0.25 M, pH 7.5-8.5, the conductivity of which is between 30 and 40 mS/cm, in particular 35 mS/cm.

Further, a washing step may be implemented right after step b) with a buffer which is advantageously identical to the loading buffer. The effectiveness of this washing step is checked through optical density measurement (OD) at a defined wavelength, for example 280 nm, which should be returned to the null value or to the baseline value. The thus-obtained fraction may be collected, as the case may be. The implementation of elution step c) may be performed with any eluant known by the skilled person in the art, allowing the protein not to be retained anymore, as an example through ionic repulsion effects or also through chaotropic effects. Preferably, the elution is performed through ionic repulsion effects. Proteins structural form and charge can be modified playing on the pH of the elution buffer, or also on the selected elution buffer.

As an example, assuming that the chromatographic support has a ligand that will be positively charged (of the anion-exchange type), reference may be made to a mixture of urea, concentration of which is between 1.2 and 8 M, and glycine, concentration of which is between 25 mM and 50 mM, said concentrations being final concentrations in the mixture. It should be pointed out that the reaction of urea with amino groups of proteins may generate some denaturation thereof and, in the presence of amino groups from exogen compounds (here the glycine), urea would then generate less denaturation of the proteins, and thus of the target protein.

Other examples of eluents include aqueous solutions of acidic pH comprised between 4 and 6, aqueous mixtures comprising the components, preferably two or three, selected from the group consisting of sodium phosphate, concentration of which is between 5 mM and 50 mM, preferably 30 mM, and ethylene glycol; sodium citrate, concentration of which is between 5 mM and 50 mM, preferably 30 mM, and ethylene glycol; sodium phosphate, concentration of which is between 5 mM and 50 mM, preferably 30 mM, and ethylene glycol; TRIS/NaCl and a calcium salt, concentration of which is between 1 mM and 10 mM, preferably 5 mM, and ethylene glycol; sodium caprylate, concentration of which is between 10 mM and 100 mM, preferably 30 mM, and ethylene glycol;

An aqueous mixture, the conductivity of which, as a result of the presence of compounds, is lower than 3 mS/cm, such as a 30 mM sodium phosphate solution, may also be used. The above concentrations are the final concentrations in the mixture. For the above binary mixtures containing ethylene glycol, the volumic proportion of ethylene glycol is especially between 20 and 70%.

For all of these buffers containing the ethylene glycol, it may be replaced by propylene glycol, which is less toxic, or by any other solvent. Urea may advantageously be used as an elution agent in the presence of amino acids, (final concentrations of which are varying from 1.2 to 8 M for urea and from 25 to 50 mM for glycine or for any other amino acid), this solution, because of its chaotropic power, makes it possible to suppress the interactions between the ligand and the adsorbed proteins. The pH of the aqueous mixtures is very preferably between 7 and 8.5, too acid pH may cause denaturation of the considered protein, and may thus result in insoluble proteins.

These aqueous mixtures may also contain from 0.5% to 1.5%, and in particular 1%, of a non-ionic detergent, as, preferably, Triton® X100. The Applicant has observed that, in some implementations, the presence of such a detergent with a pH value between 7 and 8.5, may improve the recovery yield of the eluted protein. It is also possible to use water and preferentially, WFI (bi-distilled water for injection). In one particular embodiment, when the pH for the implementation of step b) is between 5 and 8.5, the elution may be performed by lowering the pH to a value below the pKa of the ligand, if the latter is lower than the isoelectric point of the protein, or else by lowering the pH to a value below the isoelectric point of the protein, if the latter is lower than the pKa of the ligand.

At the conclusion of the elution of the fraction containing the desired protein, a purification step is still necessary in order to remove the contaminant proteins—such as lactoferrin, lactalbumin, transferrin, albumin, and immunoglobulins—from the milk. Such purification means are well known to those skilled in the art. As examples, reference may be made to affinity chromatography, hydrophobic chromatography, cation- or anion-exchange chromatography, or size-exclusion chromatography, which list is not limitative. Step d) also makes it possible, advantageously, to achieve good renaturing of the target proteins, i.e. proper folding, thus imparting to the protein a biological activity which is equivalent to that of the native protein.

Optionally, renaturing may also be performed through simple dialysis or diafiltration, in order to remove the denaturing agent. The various chromatographic steps are carried out with any, standard chromatographic apparatus, notably comprising a pumping device, and a detection system, in particular through UV-visible absorption. At the conclusion of this step for removing the last lactic proteins present in the fraction containing the desired protein, a fraction is recovered that contains the purified desired protein.

The means for recovering the fraction containing the desired protein are well known to those skilled in the art. As examples, reference may be made to affinity chromatography, hydrophobic chromatography, cation- or anion-exchange chromatography, or size-exclusion chromatography, using the commonly used eluents. In one embodiment of the invention, a step consisting of clarifying the milk is preferably performed after the skimming and defatting step (step a)) and prior to step b). The term "clarification" of the milk should be understood as referring to a step consisting of removing the micelles via disruption, thereby obtaining a clarified milk serum containing the caseins, the lactoserum proteins, and the desired protein.

This embodiment makes it possible to obtain better yields, because in this case, the desired proteins associated with the casein micelles are capable of enriching the purified fraction, which is not the case in the embodiment that does not include a clarification step, in which the micelles are removed, carrying with them the desired proteins that are associated with them. This embodiment also makes it possible to perform a submicron filtration for removing any microbial or cellular agents and cell debris present in the milk (such as bacteria, epithelial cells, or milk lymphocytes). More particularly, the milk clarification step takes place via the addition of a chelating agent at a concentration such that after mixing with the milk, the micellar structure of the milk disappears, giving clarified milk (caseins in solution or lactoserum). Clarification of the milk using chelating agents is well known to those skilled in the art. As an example of a chelating agent, reference may be made to trisodium citrate or EDTA. For example, a final sodium citrate concentration of 0.25 M provides a complete clarification of the milk.

In another embodiment of the invention, after the skimming and defatting step (step a)) and prior to step b), the casein subunit clusters are precipitated, notably through filtration or centrifugation according to usual implementations. Although optional, this step makes it possible to destabilise, via precipitation, the colloidal state of the milk. The desired proteins are released or dissociated from the casein micelles or subunits, thereby making it possible to recover the proteins associated with the micelles.

In one particular embodiment of the invention, the ligand that is simultaneously hydrophobic and ionic is 4-mercapto-ethyl-pyridine. One example of a support containing this ligand is MEP HyperCel® gel (Ciphergen®). As an example, conditions allowing adsorption of the desired protein to occur on such a support may include a pH value that is at least 0.5 pH unit above the isoelectric point of the protein (negative charge on the protein) and at least 1 pH unit below the pI of the ligand (positive charge on the gel). If the desired protein is FVII, then the selected pH may be of 8. The absorption of the protein on the ligand preferably takes place under pH conditions such that the interactions between the protein and the ligand are essentially hydrophobic. This pH is preferably between 5 and 8.5.

In the particular embodiment of the invention in which the protein to be purified is factor VII, the elution may take place by lowering the pH to a pH that is lower than the pKa of the ligand, i.e. lower than 4.8. If the ligand is 4-mercapto-ethyl-pyridine, the elution step c) can be performed using aqueous solutions and mixtures described above, at a pH which is higher than the pKa of the ligand, i.e. higher than 4.8, notably at a pH which is higher than 6 and lower than 9, and very advantageously comprised between 7.0 and 8.5, and also with water, and preferably with WFI (bi-distilled water for injection). In that case, the protein is for example factor VII.

Furthermore, the present applicant has discovered, surprisingly, that MEP HyperCel® gel, having a ligand of the 4-mercapto-ethyl-pyridine type, or the Hitrap IgY gel, having a ligand of the 2-mercaptopyridine type, displays a certain degree of selectivity with regard to FVII, whose structure is "consistent" with the reference molecule, i.e. capable of being activated. In fact, with regard to the forms that are not adsorbed on this gel, the present applicant has observed, on a regular basis, a divergence between the forms that are capable of being activated (amidolytic FVII assay) and the whole forms (antigen FVII assay). The amidolytic FVII assay is comparable to an in vitro activation of the antigens, with 1 plasma antigen unit yielding, by definition, 1 amidolytic unit, such that the activity ratio is 1. The protein may undergo multiple instances of physico-chemical or biochemical denaturation during the purification processes. This ratio is considered normal when it is between 0.8 and 1.2, and it is advantageously equal to 1. In transgenic animals, the lactic secretion of factor VII is not 100% homogeneous, and those skilled in the art are aware of the differences in the post-translational transformations, including, in particular, the glycosylation and folding of the three-dimensional structure of the proteins. Thus, the mammary cells produce FVII after transgenesis, and said FVII is glycosylated and then folded before being secreted by the mammary gland into the milk. There is no guarantee that 100% of the molecules that are created will be functional. It is likely that the control mechanisms that are naturally involved will be modified in the transgenic cell; in particular, differences in the maturation of the glycoforms in the transgenic proteins have been observed in comparison with the natural proteins.

Thus, the forms of FVII that are not adsorbed on the MEP HyperCel® gel, having a ligand of the 4-mercapto-ethyl-pyridine type, or the Hitrap IgY gel, having a ligand of the 2-mercaptopyridine type, have a ratio of 0.4 to 0.5, and the eluted forms have a ratio of 1.0 to 1.4. Therefore, the MEP HyperCel® gel selects, by adsorption, the antigen forms that are most similar to the natural forms, and it can be hypothesised that, conversely, the unbound forms may exhibit defects in fabrication by the transgenic animal. This is a definite advantage, because the objective is to extract, from the milk, human FVII that can be injected into human beings with no notable side effects, and for this purpose, FVII should be as similar as possible to the natural forms. The amidolytic/antigen activity ratio is a tool showing whether this condition is achieved.

In another particular embodiment of the invention, the ligand that is simultaneously hydrophobic and ionic is mercapto-benzimidazole sulfonic acid. One example of the support that contains this ligand is MBI HyperCel® gel (Ciphergen®), or Capto-MMC (GE Healthcare). When this type of support is used, it is appropriate to employ retention conditions (step b) that are slightly more acid, with a pH value of between 5 and 6. At such pH values, the solubility of the caseins is low, and precipitation may even start to occur. The addition of salts, such as 1M NaCl, makes it possible to keep the caseins soluble between pH 5 and pH 6. The elution may take place with aqueous solutions and mixtures previously defined.

The step d) is advantageously implemented via anion-exchange chromatography, in particular through the implementation of a strong-base type anion exchange support, i.e. with quaternary ammonium groups of —NR3+ type, R being an alkyl group such as methyl or ethyl. Such supports, commercially available, may be suited for the implementation of this step. The advantageously low ionic strength and the pH render the anion-exchange step particularly appropriate, inasmuch as it allows the desired molecule, i.e. FVII, to be concentrated and converted into activated factor VII, and then purified via conformational elution (i.e. a change in form that is specifically linked to calcium binding, which produces a change in charge in the N-terminal portion (gla domains), such that the overall protein charge becomes negative after a calcium saturation). In step d), which preferably takes place by means of anion-exchange chromatography, the elution of the protein is advantageously performed using a calcium ion solution, the concentration of which is comprised between 1 and 50 mM, preferably between 2 and 25 mM, more preferably between 3 and 12.5 mM, or between 4 and 6 mM, the source of calcium ions being for example provided by the calcium chloride. Advantageously, at step d), the elution of the protein is performed with a 5 mM calcium ions solution.

In another embodiment, the solution used for the elution may be based on copper, zinc, or manganese salts. The process according to the invention may be implemented for the extraction of a recombinant protein or for the extraction of a protein that is naturally present in the milk of the mammal in question. The protein may be a protein that is naturally present in milk, and may be, for example, β-lactoglobulin, lactoferrin, α-lactalbumin, or proteose peptones, or a mixture thereof. The protein may also be a protein that is not naturally present in milk. Examples include factor VII, factor VIII, factor IX, factor X, alpha-1 antitrypsin, antithrombin III, albumin, fibrinogen, insulin, myelin basic protein, pro-insulin, tissue plasminogen activator, and antibodies.

In one preferred embodiment, the protein is a recombinant protein and the milk that contains it is a transgenic milk. In fact, proteins that are not naturally present in milk can be synthesised in it by non-human transgenic mammals, through the use of recombinant DNA and transgenesis techniques. These techniques, which are well known to those skilled in the art, make it possible to synthesise any desired protein in the milk of a transgenic animal. Such a protein is then a recombinant or transgenic protein, inasmuch as these two terms are treated as equivalent in the present application, and is then synthesised through the use of recombinant DNA techniques.

The term "transgenic animal" should be understood as referring to any non-human animal into whose genome a fragment of exogenous DNA has been incorporated, including, in particular, a fragment that codes for a desired protein, such that the animal in question expresses the protein encoded by the exogenous DNA and can transmit the exogenous DNA to its offspring. Accordingly, any non-human mammal is suitable for the production of such a milk. Advantageous use may be made of the rabbit, ewe, goat, cow, sow, and mouse, which list is not limitative.

The secretion of the desired protein by the mammary glands, leading to its secretion in the milk of the transgenic mammal, implies control of the expression of the recombinant protein in a tissue-dependent manner. Such control methods are well known to those skilled in the art. Control of the expression is achieved through sequences that lead to the expression of a protein in a particular animal tissue. These sequences include, in particular, the promoter sequences, as well as their signal peptide sequences. Examples of promoters that are well known to those skilled in the art include the WAP (whey acidic protein) promoter, the casein promoter, and the β-lactoglobulin promoter, which list is not limitative.

A method for producing a recombinant protein in the milk of a transgenic animal may include the following steps: A synthetic DNA molecule containing a gene that codes for a desired protein, which gene is controlled by a promoter of a protein that is naturally secreted in milk, is transferred into an embryo of a non-human mammal. The embryo is then introduced into a female mammal of the same species, which then gives birth to a transgenic animal. Once the subject is sufficiently developed, lactation of the mammal is induced and the milk is collected. The milk then contains the desired recombinant protein. One example of a process for the preparation of a protein in the milk of a female mammal other than a human being is provided in document No. EP 0 527 063, whose teaching may be applied to the production of the desired protein according to the invention.

A plasmid containing the WAP promoter is constructed through the introduction of a sequence containing the promoter for the WAP gene, and this plasmid is created in such a way that it can receive a foreign gene that is rendered dependent upon the WAP promoter. The gene that codes for a desired protein is incorporated and rendered dependent upon the WAP promoter. The plasmid containing the promoter and the gene that codes for the desired protein are used to obtain transgenic animals, such as rabbits, via microinjection into the male pronucleus of rabbit embryos. The embryos are then transferred to the oviduct of hormonally prepared females. The presence of the transgenes is detected via Southern blotting, using DNA extracted from the young transgenic rabbit produced. The concentrations in the animals' milk are evaluated using specific radioimmunological assays.

The protein is advantageously a coagulation protein. The protein according to the invention is advantageously selected from factor II (FII), factor VII (FVII), factor IX (FIX), and factor X (FX), as well as their activated forms; and C protein, activated C protein, S protein, and Z protein, or mixtures thereof. In a particularly advantageous manner, the protein according to the invention is FVII or activated FVII (FVIIa).

In this regard, the FVII or FVIIa may be produced in accordance with the teaching of document No. EP 0 527 063, a summary of which method was provided above. A DNA fragment whose sequence is that of human FVII is then placed under the control of the WAP promoter. For example, such a DNA sequence appears in sequence No. 1b, as described in document No. EP 0 200 421.

The FVII according to the invention is advantageously activated. The FVIIa is obtained in vivo through cleavage of the zymogen by various proteases (FIXa, FXa, and/or FVIIa) into two chains that are connected by a disulfide bridge. The FVIIa alone has very little enzymatic activity, but when complexed with its cofactor (the tissue factor (FT)), it triggers the coagulation process by activating the FX and the FIX. The coagulant effect of the FVIIa is from 25 to 100 times greater than that of the FVII when they interact with the tissue factor (FT).

In a particularly advantageous manner, the protein is factor VII (factor VII). In one embodiment of the invention, the FVII may be activated in vitro by factors Xa, VIIa, IIa, IXa, and XIIa. The FVII according to the invention may also be activated during its purification process.

Another objective of the invention is the use of a glass filter with a positive zeta potential for the simultaneous skimming and defatting of a mammalian milk. Such implementation advantageously replaces the classical separation by centrifugation which is time consuming or the use of specific solvents for defatting (chloroform or fluoroalkane derivatives, like freon) which is a problem for use in an industrial scale. Another objective of the invention is the use of a support onto which is grafted a ligand that is simultaneously hydrophobic and ionic, for the extraction of the protein that is present in skimmed and defatted milk. Other aspects and advantages of the invention will be described in the following examples, which are provided for illustration only and do not limit the scope of the invention.

DESCRIPTION OF THE FIGURE

FIG. 1: Elution buffer tests on MEP HyperCel® gel.

EXAMPLES

Example 1

Production of Transgenic Rabbits Producing a Human FVII Protein in their Milk

First, a p1 plasmid was prepared by introducing the BamH1-Hind III sequence (a 6.3 Kb fragment) of the WAP gene (described in the paper by Devinoy et al., *Nucleic Acids Research*, vol. 16, no. 16 (Aug. 25, 1988, page 8180) into the polylinker of the p-poly III-I vector (described in the paper by Lathe et al., *Gene* (1987) 57, 193-201), between the Bam H1 and Hind III sequences. During this cloning, the BamH1 site was deleted and replaced by the ClaI site that appears in the p1 vector. Thus, the p1 vector is a plasmid that can receive a foreign gene placed under the control of the 6.3 Kb WAP promoter. The foreign gene can be introduced, for example, into the SalI site of the polylinker. The inserts containing the entirety of the promoter and the foreign genes can be isolated from the plasmid after cleavage at the two Not1 sites located at the ends of the p-poly III-I plasmid polylinker.

The p2 plasmid, obtained from the p1 plasmid, contains the promoter for the rabbit WAP gene (6.3 Kb) and the human FVII gene. The fragment used to obtain the transgenic rabbits is located between the two Not1 sites. A HindIII site was introduced into the gene leader sequence via site-directed mutagenesis in order to serve as a cloning site.

The transgenic rabbits were obtained via the classical microinjection technique (Brinster et al., *Proc. Natl. Acad. Sci. USA* (1985) 82, 4438-4442). One or two p1 plasmids containing 500 copies of the gene were injected into the male pronucleus of mouse embryos. The constructions were created in the p-poly III-I vector (Lathe et al., *Gene* (1987) 57, 193-201). The Not1-Not1 fragments of this vector containing the recombined genes were microinjected. The embryos were then transferred to the oviduct of hormonally prepared adoptive females. Approximately 10% of the manipulated embryos gave birth to young rabbits, and 2 to 5% of the manipulated embryos gave birth to young transgenic rabbits. The presence of the transgenes was detected via Southern blotting, using DNA extracted from the tails of the rabbits. The FVII concentrations in the animals' blood and milk were evaluated using specific radioimmunological assays.

The biological activity of the FVII was evaluated by adding milk to a cell culture support or to a rabbit mammary explant culture support. The technique used to obtain transgenic rabbits that produce, in their milk, the FVII according to the invention is described in greater detail in European patent No. EP 0 527 063.

Example 2

Preparation of a Skimmed and Defatted Fraction

Because the raw material consists of raw rabbit milk (that is, non-skimmed frozen milk) containing approximately 150 grams per liter of proteins and a comparable amount of lipids (15% cream), it is necessary first of all to "fluidise and de-fat" the medium in order to render it compatible with the chromatographic conditions. To do so:
one volume of thawed raw milk was mixed with two volumes of an aqueous solvent,
the fully fluid mixture was filtered through a glass fiber support with a positive zeta potential, i.e. an Ultipor GF Plus filter (manufactured by Pall Life Science).
The result was a fully fluid raw material that was sufficiently defatted for use with chromatographic techniques.
Protocol "A":
The aqueous solvent was a phosphate solution with low ionic strength (less than 100 mM), with or without the addition of sodium chloride.
Protocol "B":
The solvent contained a chelating agent such as trisodium citrate or EDTA at a concentration such that, after mixing with the milk, the micellar structure of the milk disappeared, leaving so-called "clarified" milk (caseins in solution or lactoserum). For example, a final sodium citrate concentration of 0.25 M at a pH of 8.0 provided a complete clarification of the milk.

Example 3

Affinity Chromatography of the Skimmed and Defatted Fractions According to Protocol "A" in Example 2

The capture of transgenic or recombinant FVII (rFVII) in milk stabilised on MEP-HyperCel gel was demonstrated using the following assays, in which:

a) Volume Of The MEP Gel=2 mL/Volume Of Raw Milk F1=4 mL

Ratio of the volume of milk to the volume of MEP gel=2
In this example, 427 ml of milk were mixed with 3843 ml (mixture 1:9) of sodium phosphate buffer 0.015M et pH 8.27 with a conductivity of 4.5 mS/cm at 25° C. The mixture was filtered on a filter Utripor GF+ with a 1 µm threshold, giving 4240 ml of clarified milk for subsequent chromatography, the pH of the clarified milk being 8.2 and the conductivity 8 mS/cm at 25° C. 40 ml of this solution (corresponding to 4 ml of raw milk) were injected on the gel, once conditioned in a 1.1 cm diameter column. The height of the stabilised gel bed is 2 cm, thus providing with 2 ml of packed gel (ratio raw milk/gel=2).

Before injecting the biological material, the gel is equilibrated with a 25 mM sodium phosphate solution containing 40 mM sodium chloride at pH 8.2, the conductivity of which is of 8 mS/cm at 25° C. (loading buffer). The flow rate of the pump is adjusted to 1.5 ml/minute, i.e. an estimated contact time in the gel of about 1 minute E/E (Entry/Exit).

The column is connected to a 280 nm UV lamp detector and the optical density signal is continuously registered on paper. 40 ml of biological material are injected, and a sample "MEP start" is set aside for analysis. Following the injection, the gel is washed with the 25 mM sodium phosphate loading solution containing 40 mM sodium chloride, about 8.5 ml of which are required for re-obtaining the baseline on the OD recorder at 280 nm. 48.3 ml of non-absorbed protein fraction called "non-retained MEP" are collected. Three successive elutions are performed.
Solution A=giving 20.6 ml of MEP-eluate 1
→80% loading buffer+20% ethylene glycol
Solution B=giving 17 ml of MEP-eluate 2
→50% loading buffer+50% ethylene glycol
Solution C=giving 9 ml non tested
→Loading buffer adjusted to pH 3 with glacial acetic acid.

The gel is then regenerated with NaoH 1M, and conserved in 1M sodium chloride medium containing 20% ethanol (v/v).
The analytical data are gathered in the herein below table.

| Fractions | Volume (mL) | FVII antigen concentration (IU/mL) | Amount of FVII antigen (IU) | Yield (%) |
|---|---|---|---|---|
| Initial MEP | 40 | 22.2 | 887 | 100% |
| Unbound MEP | 48.3 | 5.6 | 269 | 30% |
| eluate1-MEP (20% EG) | 20.6 | 6.4 | 131 | 15% |
| eluate2-MEP (50% EG) | 17.0 | 23.0 | 390 | 44% |

Conclusions:

Thirty percent (30%) of the FVII was not retained by the gel, and the total of the eluates represented 59% of the FVII employed. According to the results (89%), approximately 10% of the FVII was not recovered.

b) 1 Volume Of The MEP Gel=10 mL/Volume of F1 Raw Milk=200 mL

The ratio of the volume of milk to the volume of MEP gel was increased from 3 to 20, with fractionation by 100 mL increments.

| Fractions | Volume (mL) | FVII antigen concentration (IU/mL) | Amount of FVII antigen (IU) | Yield (%) |
|---|---|---|---|---|
| Initial MEP | 624 | 91.3 | 56,971 | 100% |
| Unbound 1 | 100 | 20.6 | 2,057 | 22.5% |
| Unbound 2 | 100 | 23.7 | 2,394 | 26.2% |
| Unbound 3 | 100 | 28.9 | 2,914 | 31.9% |
| Unbound 4 | 100 | 28.5 | 2,967 | 32.5% |
| Unbound 5 | 100 | 32.2 | 3,247 | 35.6% |
| Unbound 6 | 130 | 35.7 | 4,644 | 41% |
| Unbound, pool | 637 | 28.6 | 18,222 | 32% |
| Eluate-MEP (50% EG) | 130 | 156.3 | 20,323 | 36% |

Conclusions:

Thirty-two percent (32%) of the FVII was not retained by the gel as a function of the charge of the gel (22 to 41%). The optimal milk-to-gel ratio was from 10 to 15. The eluate (50% EG in 30 mM phosphate, pH 8) represented 44% of the FVII employed. According to the results (68%), 30% of the FVII was not recovered, which indicates that the captured form is highly hydrophobic. These two assays, which were performed on second-generation (so-called "$F_1$") transgenic rabbit milk, indicate that approximately 30% of the rFVII was not adsorbed on the so-called "mixed-mode" MEP-HyperCel gel.

Supported Results for MEP-HyperCel:

Here, the objective was to support the preliminary results for first-generation (so-called "$F_0$") transgenic rabbit milk and to re-treat the fractions that were "unbound" on MEP-HyperCel gel, according to either Protocol "A" (stabilised casein micelles) or Protocol "B" (solubilised caseins).

a) 1 Volume of The MEP Gel=10 mL/Volume of F0 Raw Milk=133 mL

Ratio of the volume of milk to the volume of MEP gel=13.3

Initial treatment of the raw milk according to Protocol "A"

| Fractions | Volume (mL) | FVII antigen concentration (IU/mL) | Amount of FVII antigen (IU) | Yield (%) |
|---|---|---|---|---|
| Initial MEP | 400 | 97.8 | 39,104 | 100% |
| Unbound, MEP 1 | 421 | 43.1 | 18,145 | 46% |
| Eluate-MEP1 (50% EG) | 163.5 | 45.5 | 7,439 | 19% |

Re-treatment of Unbound-1 according to Protocol "A" (stable micelles)

| Unbound, MEP 2 | 444 | 29.2 | 12,969 | 71% |
|---|---|---|---|---|
| Eluate-MEP2 (50% EG) | 100 | 19.6 | 1,955 | 11% |

Conclusions:

Forty-six percent (46%) of the FVII was not retained by the gel after the first passage. This proportion rose to 71% for the second passage. The $F_0$ milk yielded a greater proportion of this form than did the $F_1$ milk.

Conversely, 19% of the FVII was eluted during the first passage (MEP1 result=65%) and 11% was eluted during the second passage (MEP2 result=82%). Overall (MEP1+2), 33% of the FVII remained unbound, in comparison with 24% of the FVII bound and eluted in EG. According to the results (57%), approximately 40% of the FVII was not recovered, which indicates that the retained form was highly hydrophobic.

b) Volume of The MEP Gel=10 mL/Volume of F0 Raw Milk=140 mL

Ratio of the volume of milk to the volume of MEP gel=14

Initial treatment of the raw milk according to Protocol "A"

| Fractions | Volume (mL) | FVII antigen concentration (IU/mL) | Amount of FVII antigen (IU) | Yield (%) |
|---|---|---|---|---|
| Initial MEP | 390 | 109 | 42,393 | 100% |
| Unbound, MEP 1 | 425 | 45.5 | 19,316 | 46% |
| Eluate-MEP1 (50% EG) | 155 | 45.3 | 7,014 | 17% |

Re-treatment of Unbound-1 according to Protocol "B" (destabilised micelles)

| Unbound, MEP 2 | 609 | 14.2 | 8,642 | 46% |
|---|---|---|---|---|
| Phosphate eluate (30 mM, pH 8) | 91 | 39.5 | 3,595 | 19% |
| Eluate-MEP2 (50% EG) | 98 | 27.9 | 2,733 | 14% |

Conclusions:

Forty-six percent (46%) of the FVII was not adsorbed onto the gel after the first passage. This proportion remained at 46% during the second passage, after "clarification of the milk" with a sufficient quantity of citrate for a concentration of 0.25 M. When the gel was washed with a 30 mM phosphate buffer (washing after injection), a FVII elution was found to represent 19% of the total. This elution clearly reflected a less hydrophobic form of FVII.

A total of 17% of the FVII was eluted during the first passage (MEP1 result=63%) and 14% was eluted during the second passage (MEP2 result=79%). Overall (MEP1+2), 29% of the FVII was not retained or was prematurely eluted, in comparison with 23% of the FVII adsorbed and eluted in EG. According to the results (52%), approximately 40% of the FVII was not retained, which indicates that the retained form was highly hydrophobic.

Example 4

Elution Buffer Tests on MEP HyperCel® Gel

Here, the objective was to improve the elution yield by testing a combination of ethylene glycol and various adjuvants.

|  | Ethylene glycol | pH | Detergent | Solvent | Salts | Yield |
|---|---|---|---|---|---|---|
| 1 (standard) | 50% | 7.0 | — | — | 30 mM sodium phosphate | 26% |
| 2 | 50% | 6.0 | — | — | Citrate/30 mM citric acid | 10% |
| 3 | 50% | 5.0 | — | — | Citrate/30 mM citric acid | 2% |
| 4 | 50% | 4.0 | — | — | Citrate/30 mM citric acid | 7% |
| 5 | 50% | 3.0 | — | — | Citrate/30 mM citric acid | 20% |
| 6 | 50% | 7.5 | 1% | — | 30 mM sodium phosphate | 31% |
| 7 | 50% | 6.0 | — | — | Tris/NaCl + 5 mM calcium | 9% |
| 8 | 70% | 6.0 | — | — | Citrate/30 mM citric acid | 29% |
| 9 | 50% | 7.2 | — | — | 30 mM sodium caprylate | 31% |
| 10 | — | 8.0 | 1% | 0.3% | 30 mM sodium phosphate | 7% |

The addition of a non-ionic detergent (Triton X100) and a basic pH appeared to improve the elution yield. The tests also included replacing the ethylene glycol ($CH_2OH$—$CH_2OH$) with propylene glygol ($CH_2OH$—$CH_2$—$CH_2OH$), which is less toxic, and a test in urea ($NH_2$—CO—$NH_2$), a denaturing agent, with renaturing at a concentration of 6 M.

Various elution methods were also tested, with the following results:

MEP-HyperCel elution with 50% ETHYLENE GLYCOL (v/v)
Injection: Milk clarified with sodium citrate (0.25 M)
Contact time on MEP gel: 1.7 minutes (not optimised)
Elution: Mixture: 50% ethylene glycol+1% Triton X100+ 49% 15 mM sodium phosphate, pH 8

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered Clarified milk, GF + 0.45 μm | 8,642 | 100% | 27,910 (14 mg) | 100% | 0.16% |
| Unbound on MEP-HyperCel | 8,496 | 98% | 10,614 (5.3 mg) | 38% | 0.06% |
| MEP-HyperCel eluate | 238 | 3% | 12,256 (6.1 mg) | 44% | 2.6% |
| MEP results |  | 101% | MEP results | 82% |  |

Note:
1 IU of FVII:Ag = 0.5 μg/mL of FVII (standard plasma)

MEP-HyperCel elution with 50% PROPYLENE GLYCOL (v/v)
Injection: Milk clarified with sodium citrate (0.25 M)
Contact time on MEP gel: 8 minutes (optimised)
Elution: Mixture: 50% propylene glycol+1% Triton X100+ 49% 15 mM sodium phosphate, pH 8

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered clarified milk, GF + 0.45 μm | 8,500 | 100% | 21,600 (10.8 mg) | 100% | 0.13% |
| Unbound on MEP-HyperCel | 8,250 | 97% | 3,220 (1.6 mg) | 15% | 0.02% |
| MEP-HyperCel eluate | 412 | 5% | 11,039 (5.5 mg) | 51% | 1.3% |
| MEP results |  | 101% | MEP results | 66% |  |

Note:
1 IU of FVII:Ag = 0.5 μg/mL of FVII (standard plasma)

MEP-HyperCel elution with 6M UREA
Injection: Milk clarified with sodium citrate (0.25 M)
Contact time on MEP gel: 1.7 minutes
Elution: Mixture: 6M urea+20 mM glycine+50 mM HEPES (N-2-Hydroxyethylpiperazine-N'-2-ethanesulfonic acid) buffer, pH 8.2

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered clarified milk, GF + 0.45 μm | 9,210 | 100% | 27,262 (14.1 mg) | 100% | 0.15% |
| Unbound on MEP-HyperCel | 9,086 | 99% | 12,945 (6.5 mg) | 47% | 0.07% |
| MEP-HyperCel eluate | 178 | 2% | 11,955 (6 mg) | 44% | 3.3% |
| MEP results |  | 101% | MEP results | 91% |  |

Note:
1 IU of FVII:Ag = 0.5 μg/mL of FVII (standard plasma)

MEP-HyperCel elution with 2M UREA
Injection: Milk clarified with sodium citrate (0.25 M)
Contact time on MEP gel: 8 minutes
Elution: Mixture: 2M urea+20 mM glycine+50 mM HEPES buffer, pH 8.2

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered clarified milk, GF + 0.45 μm | 8,931 | 100% | 26,037 (13.5 mg) | 100% | 0.15% |

-continued

| Fraction | Amount of proteins (mg) | Protein distribution (%) | Amount of FVII:Ag (IU & mg) | FVII antigen yield (%) | Purity of FVII (%) |
|---|---|---|---|---|---|
| Unbound on MEP-HyperCel | 8,790 | 98% | 4,389 (2.2 mg) | 17% | 0.02% |
| MEP-HyperCel eluate | 320 | 4% | 17,963 (9 mg) | 69% | 2.8% |
| | MEP results | 102% | MEP results | 86% | |

Note:
1 IU of FVII:Ag = 0.5 µg/mL of FVII (standard plasma)

MEP-HyperCel elution with 0.5M UREA

Injection: Milk clarified with sodium citrate (0.25 M)

Contact time on MEP gel: 8 minutes

Elution: Mixture: 0.5M urea+20 mM glycine+50 mM HEPES buffer, pH 8.2

| Fraction | Amount of proteins (mg) | Protein distribution (%) | Amount of FVII:Ag (IU & mg) | FVII Antigen yield (%) | Purity of FVII (%) |
|---|---|---|---|---|---|
| Filtered clarified milk, GF + 0.45 µm | 1,155 | 100% | 3,440 (1.7 mg) | 100% | 0.15% |
| Unbound on MEP-HyperCel | 1,129 | 98% | 241 (0.12 mg) | 7% | 0.01% |
| MEP-HyperCel eluate | 21.7 | 2% | 1,533 (0.77 mg) | 45% | 3.5% |
| | MEP results | 102% | MEP results | 52% | |

Note:
1 IU of FVII:am = 1 IU of functional FVII:Ag, or approximately 0.5 µg/mL of FVII (standard plasma)

MEP-HyperCel elution with no UREA

Injection: Milk clarified with sodium citrate (0.25 M)

Contact time on MEP gel: 8 minutes

Elution: Mixture: 20 mM glycine+50 mM HEPES buffer, pH 8.2

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered clarified milk, GF + 0.45 µm | 1,733 | 100% | 4,442 (2.2 mg) | 100% | 0.13% |
| Unbound on MEP-HyperCel | ND | NA | ND | NA | NA |
| MEP-HyperCel eluate | 45.9 | 3% | 2,496 (1.25 mg) | 56% | 2.7% |

ND = Not determined;
NA = Not applicable
Note:
1 IU of FVII:Ag = 0.5 µg/mL of FVII (standard plasma)

MEP-HyperCel acid elution (elution pH=3<pKa of MEP)

Injection: Milk clarified with sodium citrate (0.25 M)

Contact time on MEP gel: 8 minutes

Elution: 0.1M glycine+HCl in sufficient quantity for a pH of 3

| Fraction | Amount of FVII:Ag (IU & mg) | FVII antigen yield (%) |
|---|---|---|
| Filtered clarified milk, GF + 0.45 µm | 44,275 (22 mg) | 100% |
| Unbound on MEP-HyperCel | 10,081 (5 mg) | 23% |
| MEP-HyperCel eluate* | 29,364 (14.7 mg) | 66% |
| | MEP results | 89% |

*Neutralisation of the eluate through the addition of a base during the course of the elution
Note:
1 IU of FVII:Ag = 0.5 µg/mL of FVII (standard plasma)

MEP-HyperCel elution in purified water (WFI)

Injection: Milk clarified with sodium citrate (0.25 M)

Contact time on MEP gel: 8 minutes

Elution: bidistilled WFI

| Fraction | Amount of proteins (mg) | Protein distribution (%) | Amount of FVII:Ag (IU & mg) | FVII antigen yield (%) | Purity of FVII (%) |
|---|---|---|---|---|---|
| Filtered clarified milk, GF + 0.45 µm | 6,147 | 100% | 22,713 (11.4 mg) | 100% | 0.18% |
| Unbound on MEP-HyperCel | 5,929 | 96% | 3,454.5 (1.7 mg) | 15% | 0.03% |
| MEP-HyperCel eluate | 298 | 5% | 18,936 (9.5 mg) | 83% | 3% |
| | MEP results | 101% | MEP results | 99% | |

Note:
1 IU of FVII:Ag = 0.5 µg/mL of FVII (standard plasma)
FVII:Ag = Antigenic assay of FVII in an ELISA system (detection based on specific antibodies);

FVII:Ag=Antigenic assay of FVII in a ELISA system (detection based on specific antibodies);

In plasma, 1 IU/mL of FVII is equivalent to 0.5 µg/mL of pure FVII protein;

FVII:am=Coagulable FVII content, as measured after contact with the tissue factor on FVII-deficient human plasma.

The FVII (proenzyme) is converted to FVIIa (enzyme), which converts FX to FXa, which causes plasma coagulation (via the generation of thrombin, which acts on the fibrinogen). In theory, if all of the molecules (in international standard plasma) are functional, then 1 IU of FVII:Ag is approximately equal to 1 IU of FVII:am (r=100%). In this assay, if FVIIa (partially activated FVII) is already present, then the generation of FXa may be slightly accelerated (r=100% to 200%). However, if the FVII is damaged or "atypical" (no association with the tissue factor), then r<100%. The FVII:am/FVII:Ag ratio (expressed as a percentage) reflects the functional state of the FVII molecule during purification.

|  | FVII:Ag (IU/mL) | FVII:am (IU/mL) | FVII:Am/FVII:Ag (%) |  |
|---|---|---|---|---|
| Initial MEP | 38.6 | 47.4 | 123% |  |
| Unbound, MEP | 6.9 | 4.8 | 70% | Functional defect |
| MEP eluate (WFI) | 151.9 | 179.3 | 118% |  |

Conclusion:

In unbound MEP, FVII appears to exhibit a defect (in fabrication) and proteolysis.

Example 5

Treatment of MEP-HyperCel Eluates on Q-Sepharose FF

FVII divides itself into 2 forms on Q-Sepharose FF ion exchangers, i.e. an elution of almost pure FVII in 5 mM calcium (referred to as the "5 mM $Ca^{2+}$" fraction) and a low-purity FVII elution in 50 mM calcium (referred to as the "50 mM $Ca^{2+}$" fraction). The classical proportions, as observed (n=7 batches), were 36%±8% and 40%±12%, respectively.

1 Volume of QSFF Gel=10 mL

Treatment of the MEP1 eluate (first passage after treatment according to Protocol "A")

| Fractions | Volume (mL) | FVII antigen concentration (IU/mL) | Amount of FVII antigen (IU) | Yield (%) |
|---|---|---|---|---|
| MEP1 eluate fraction | 163 | 45.5 | 7,416 | 100% |
| 5 mM $Ca^{2+}$ fraction | 39 | 63.6 | 2,480 | 33% |
| 50 mM $Ca^{2+}$ fraction | 48 | 28.3 | 1,358 | 18% |

Treatment of the MEP2 eluate (second passage after treatment according to Protocol "A")

| Fractions | Volume (mL) | FVII antigen concentration (IU/mL) | Amount of FVII antigen (IU) | Yield (%) |
|---|---|---|---|---|
| MEP2 eluate fraction | 98 | 19.6 | 1,921 | 100% |
| 5 mM $Ca^{2+}$ fraction | 31 | 26.0 | 806 | 42% |
| 50 mM $Ca^{2+}$ fraction | 48 | 10.4 | 497 | 26% |

As can be seen, in both instances the predominant fraction was the "5 mM $Ca^{2+}$" fraction. Overall, 3,286 IU of "5 mM" FVII were extracted. In terms of volume of milk, this yield corresponded to 12.5 mg of rFVII per liter of milk.

1 Volume of QSFF gel=10 mL

Treatment of the MEP1 eluate (first passage after treatment according to Protocol "A")

| Fractions | Volume (mL) | FVII antigen concentration (IU/mL) | Amount of FVII antigen (IU) | Yield (%) |
|---|---|---|---|---|
| MEP1 eluate fraction | 154 | 45.5 | 7,007 | 100% |
| 5 mM $Ca^{2+}$ fraction | 50 | 71.6 | 3,574 | 51% |
| 50 mM $Ca^{2+}$ fraction | 27 | 58.4 | 1,548 | 22% |

Treatment of the MEP2 eluate (second passage after treatment according to Protocol "B")

| Fractions | Volume (mL) | FVII antigen concentration (IU/mL) | Amount of FVII antigen (IU) | Yield (%) |
|---|---|---|---|---|
| MEP2 eluate fraction | 96 | 27.9 | 2,678 | 100% |
| 5 mM $Ca^{2+}$ fraction | 29.4 | 23.1 | 679 | 25% |
| 50 mM $Ca^{2+}$ fraction | 40 | 19.1 | 764 | 28% |

As can be seen, the predominant fraction in the treatment according to Protocol "A" was the "5 mM $Ca^{2+}$" fraction, whereas the proportion changed for Protocol "B". This shows that treatment with citrate favoured the presence of the less desirable "50 mM" form. Overall, 4,253 IU of "5 mM" FVII were extracted. In terms of volume of milk, this yield corresponded to 15 mg of rFVII per liter of milk.

Example 6

Characteristics of the FVII Obtained from the MEP–HyperCel+Q-Sepharose FF 5 mM Calcium Eluate Sequence Analytical characteristics are the following:

FVII:Ag=252.9 IU/mL-Proteins=123 μg/mL (calculated purity: 98%)

T0 FVII:C=3,224 IU/mL at T0, or a ratio of 13.4

T24 at 26 h and at room temperature (RT) FVII:C=3,721 to 4,365 IU/mL, or a ratio of 15.5 to 18.2

Quality control for rFVIIa (from NovoNordisk)→ratio=21.5 to 25.1

Densitometric analysis:

At T0: 50.3% of uncleaved rFVII;

After 18 hours at room temperature: presence of 5.3% of uncleaved rFVII. The FVII obtained from the MEP+QSFF sequence yielded a highly purified FVII whose activation took place at a ratio of approximately 50%; however, this activation took place naturally and slowly in the support.

The invention claimed is:

1. A process for the extraction of factor VII present in milk, the process comprising:
   a) skimming and defatting said milk,
   b) transferring the defatted and skimmed fraction containing said factor VII to a chromatographic support onto which is grafted a mercapto-ethyl-pyridine type ligand which is simultaneously hydrophobic and ionic, under pH conditions allowing said factor VII to be captured on said support, said pH being higher than 4.6, c) eluting the factor VII, d) purifying the eluted fraction by removing the milk proteins from said eluted fraction by using a chromatography step selected from the group consisting of affinity chromatography, hydrophobic chromatography, cation-exchange chromatography, anion-exchange chromatography and size-exclusion chromatography, and e) recovering said factor VII.

2. The process according to claim 1, wherein, after the skimming and defatting step (step a) and prior to step b), a milk clarification step takes place.

3. The process according to claim 2, wherein said milk clarification step takes place via the addition of a chelating agent at a concentration such that, after mixing with said milk, the micellar structure of the milk disappears, giving clarified milk (caseins in solution or lactoserum).

4. The process according to claim 1 or 2, wherein, after the skimming and defatting step (step a) and prior to step b), the casein subunit clusters are precipitated.

5. The process according to claim 1, wherein said ligand that is simultaneously hydrophobic and ionic is 4-mercapto-ethyl-pyridine.

6. The process according to claim 1, wherein step c), consisting of eluting said protein, is performed using a mixture of urea, concentration of which is between 1.2 and 8 M, and glycine, concentration of which is between 25 mM and 50 mM.

7. The process according to claim 1, wherein step d) takes place through anion-exchange chromatography.

8. The process according to claim 7, wherein after the anion-exchange chromatography step, the elution of the protein takes place using a 1 mM to 50 mM calcium ion solution.

9. The process according to claim 1, wherein said factor VII is a recombinant protein.

10. The process according to claim 1, wherein said factor VII is an activated factor VII (factor VIIa).

11. The process according to claim 1, wherein the skimming and defatting step (step a) is performed by filtration to a glass filter with a positive zeta potential.

12. The process according to claim 1, wherein said eluting of said protein (step c) is performed using aqueous solutions of acidic pH comprised between 4 and 6, aqueous mixtures comprising the two components selected from the group consisting of sodium phosphate, a concentration of which is between 5 mM and 50 mM and ethylene glycol; sodium citrate, a concentration of which is between 5 mM and 50 mM and ethylene glycol; TRIS/NaCl and a calcium salt, a concentration of which is between 1 mM and 10 mM and ethylene glycol; and sodium caprylate, a concentration of which is between 10 mM and 100 mM and ethylene glycol.

13. The process according to claim 12, wherein said eluting of said protein (step c) is performed using aqueous solutions of acidic pH comprised between 4 and 6, aqueous mixtures comprising the two components selected from the group consisting of sodium phosphate, a concentration of which is 30 mM and ethylene glycol; sodium citrate, a concentration of which is 30 mM and ethylene glycol; TRIS/NaCl and a calcium salt, a concentration of which is 5 mM and ethylene glycol; and sodium caprylate, a concentration of which is 30 mM and ethylene glycol.

14. The process according to claim 1, wherein said eluting of said protein (step c) is performed using aqueous solutions of acidic pH comprised between 4 and 6, aqueous mixtures comprising the three components consisting of TRIS/NaCl, and a calcium salt, a concentration of which is between 1 mM and 10 mM, and ethylene glycol.

15. The process according to claim 14, wherein said eluting of said protein (step c) is performed using aqueous solutions of acidic pH comprised between 4 and 6, aqueous mixtures comprising the three components consisting of TRIS/NaCl, and a calcium salt, a concentration of which is 5 mM, and ethylene glycol.

16. The process according to claim 1, wherein said eluting of said protein (step c) is performed using an aqueous mixture, the conductivity of which, linked to the presence of compounds, is lower than 3 mS/cm, or water.

17. The process according to claim 16, wherein the water is WFI (bidistilled water for injection).

18. A process for the extraction of a protein that is present in skimmed and defatted milk, the process comprising:

a) filtering milk using a glass filter having a positive zeta potential to obtain the skimmed and defatted milk containing said protein;

b) capturing said protein on a support onto which is bound a mercapto-ethyl-pyridine type ligand or a mercaptopyridine type ligand under pH conditions wherein the ligand is simultaneously hydrophobic and ionic; and c) eluting the captured protein, wherein the captured protein is factor VII.

19. The process according to claim 18, further comprising:

d) purifying the eluted fraction by removing the milk proteins from said eluted fraction by using a chromatography step selected from the group consisting of affinity chromatography, hydrophobic chromatography, cation-exchange chromatography, anion-exchange chromatography and size-exclusion chromatography, and e) recovering said factor VII.

20. A process for the extraction of a factor VII present in milk, the process comprising:

a) skimming and defatting said milk, b) transferring the defatted and skimmed fraction containing said factor VII to a chromatographic support onto which is grafted a mercapto-ethyl-pyridine type ligand that is simultaneously hydrophobic and ionic, under pH conditions allowing said protein to be captured on said support, said pH being higher than 4.6, c) eluting the factor VII using an aqueous mixture, the conductivity of which is lower than 3 mS/cm, or WFI (bidistilled water for injection), d) purifying the eluted fraction by removing the milk proteins from said eluted fraction by using a chromatography step selected from the group consisting of affinity chromatography, hydrophobic chromatography, cation-exchange chromatography, anion-exchange chromatography and size-exclusion chromatography, and e) recovering said factor VII.

21. The process according to claim 20, wherein said ligand that is simultaneously hydrophobic and ionic is 4-mercapto-ethyl-pyridine.

22. The process according to claim 20, wherein said factor VII is a recombinant protein.

23. The process according to claim 20, wherein said factor VII is an activated factor VII (factor VIIa).

* * * * *